US00PP28247P3

(12) United States Plant Patent
Carrières

(10) Patent No.: US PP28,247 P3
(45) Date of Patent: Aug. 8, 2017

(54) APPLE TREE NAMED 'RM-1'

(50) Latin Name: *Malus domestica* (Borkh.)
Varietal Denomination: RM-1

(71) Applicant: Red Moon GmbH, Bozen (IT)

(72) Inventor: Jean-Luc Carrières, Montcuq (FR)

(73) Assignee: RED MOON GMBH, Bozen (IT)

( * ) Notice: Subject to any disclaimer, the term of this patent is extended or adjusted under 35 U.S.C. 154(b) by 0 days.

(21) Appl. No.: 14/757,215

(22) Filed: Dec. 7, 2015

(65) Prior Publication Data

US 2017/0164533 P1 Jun. 8, 2017

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — Annette Para
(74) *Attorney, Agent, or Firm* — James A. Lucas; Driggs, Hogg, Daugherty & Del Zoppo Co., LPA

(57) ABSTRACT

'RM-1' is a new and distinct apple tree notable for its upright plant habit, red skin over color, red flesh color, and late timing of fruit ripening.

5 Drawing Sheets

Latin name of the genus and species of the plant claimed: *Malus domestica* (Borkh.).
Variety denomination: 'RM-1'.

STATEMENT REGARDING FEDERALLY SPONSORED RESEARCH OR DEVELOPMENT

None

BACKGROUND OF THE INVENTION

The present invention relates to a new and distinct cultivar of apple tree, botanically known as *Malus domestica*, and hereinafter referred to by the name 'RM-1'.

The new apple variety 'RM-1' originated from an open-pollination in Lot, France of *Malus domestica* 'Zwintcher CSR 22', (not patented), as the female, or seed parent, with an unknown selection of *Malus domestica*, as the male or pollen, parent. The new Apple tree was discovered and selected by the inventors as a single plant from within the progeny of the stated open-pollination in a controlled environment in Lot, France in 2000.

Asexual reproduction of the new apple tree by budding and grafting, since 2006 in Lot, France, has demonstrated that the new variety reproduces true to type with all of the characteristics, as herein described, firmly fixed and retained through successive generations.

SUMMARY OF THE INVENTION

The following characteristics of the new variety have been repeatedly observed and can be used to distinguish 'RM-1' as a new and distinct cultivar of apple:

1. Upright plant habit.
2. Red skin over color.
3. Late timing of fruit ripening.
4. Red flesh color.

BRIEF DESCRIPTION OF THE PHOTOGRAPHS

DETAILED BOTANICAL DESCRIPTION

Figure 1:
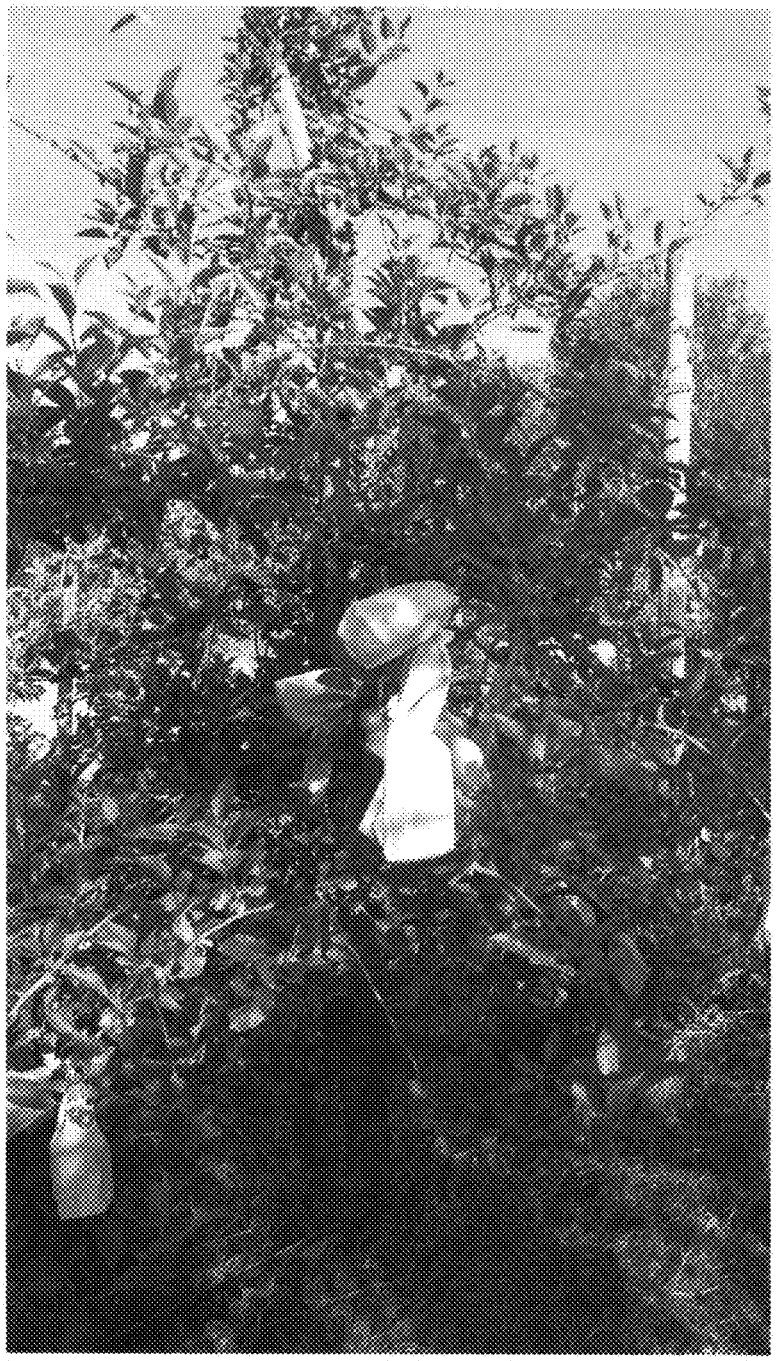
FIG. 1 shows the tree of the new variety.
Figure 2:
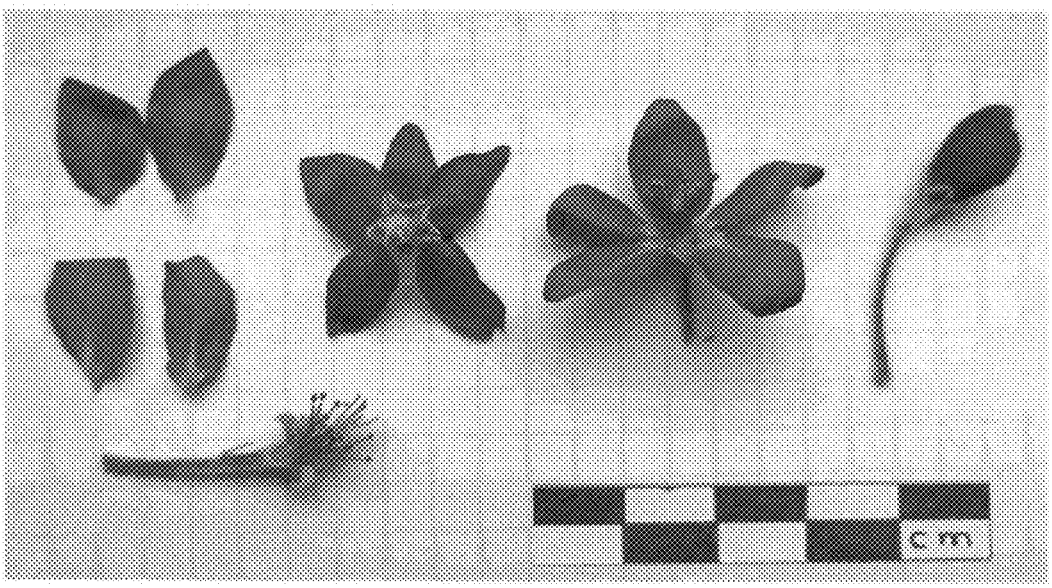
FIG. 2 shows flower of the new variety.
Figure 3:
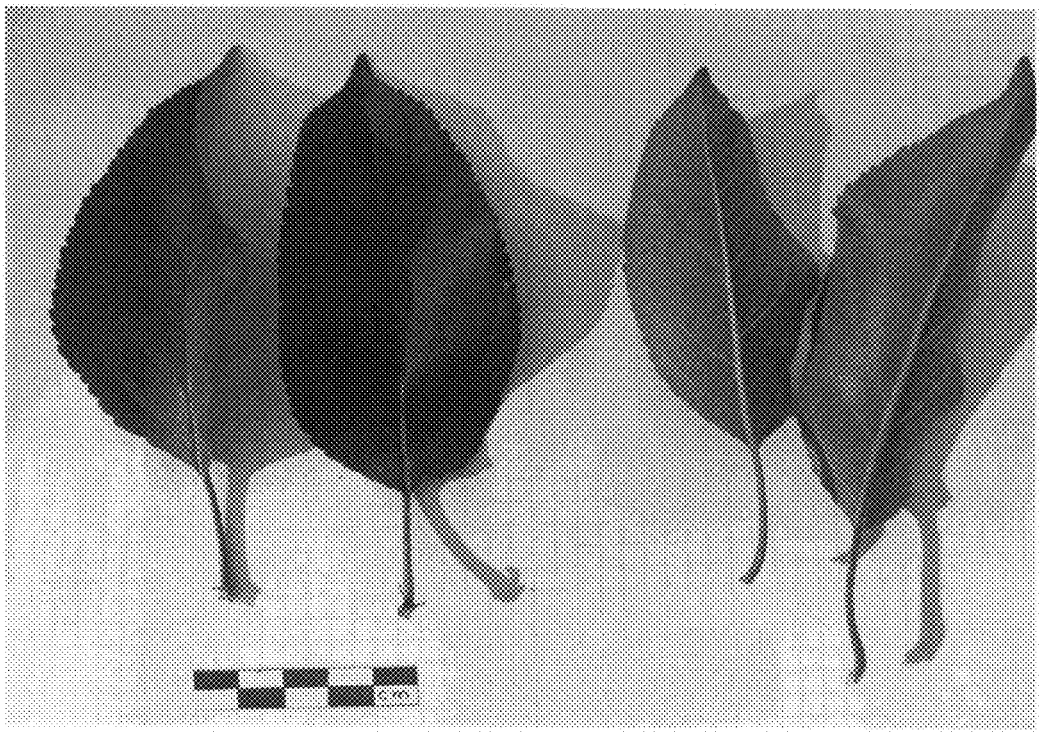
FIG. 3 shows the leaves of the new variety.
Figure 4:
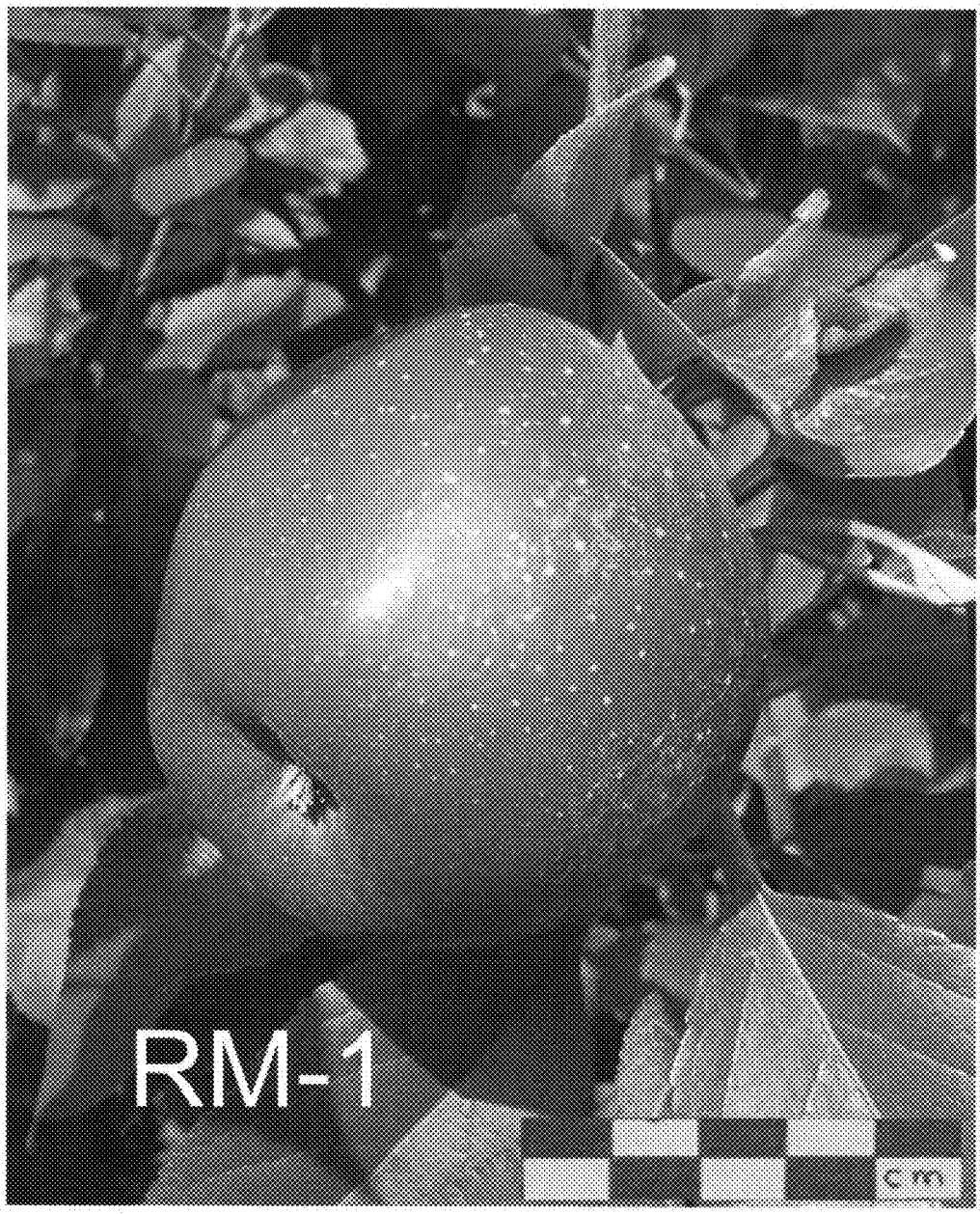
FIG. 4 shows the fruit of the new variety.
Figure 5:
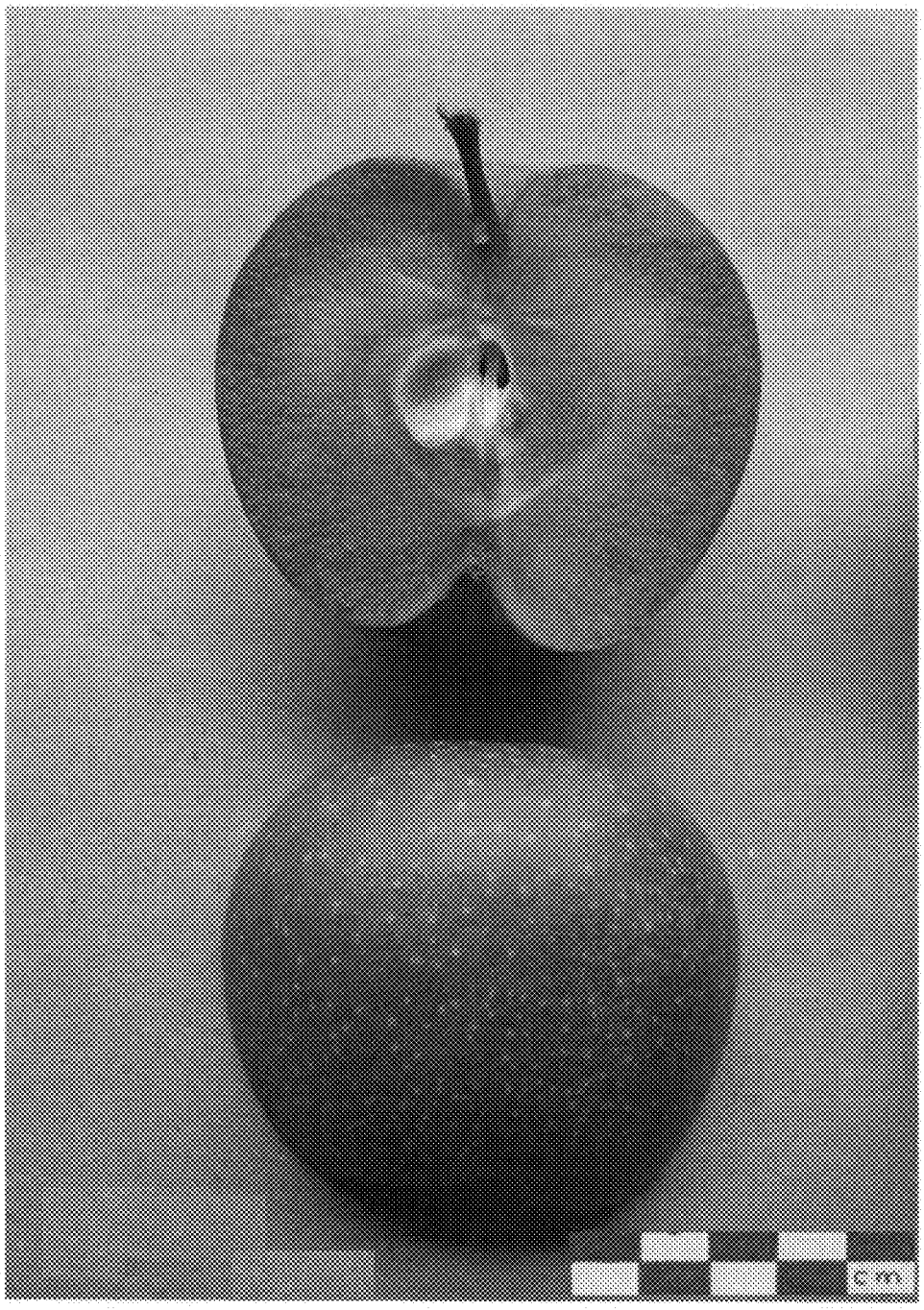
FIG. 5 shows the fruit section of the new variety.

The following detailed botanical description is based on observations of trees planted in 1995, and described during the 2013 and 2014 growing seasons at Lot, France. Color descriptions refer to The Royal Horticultural Society Colour Chart (1995). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Botanical classification: *Malus domestica* Borkh cultivar 'RM-1'.

Parentage:

*Female, or seed parent.*—*Malus domestica* 'Zwintcher CSR 22', not patented.

*Male, or pollen, parent.*—Unknown selection of *Malus domestica*, not patented.

Tree:

*Vigor.*—Vigorous.
*Habit.*—Semi-Upright.
*Size.*—Height: 3.0 m.
*Trunk.*—Diameter: 18-22 cm at 30 cm above graft union; bark texture smooth; color brown RHS 200C.
*Branches.*—1 m above graft union; length 170 cm; diameter 8.0 cm; crotch angle 60'; color light brown RHS 200D.

Dormant one year old shoot:

*Size.*—Diameter 5-6 mm; Length 25-30 cm.
*Color.*—Brown RHS 200C.
*Internode length.*—2.0 cm.
*Pubescence.*—Few.
*Lenticels.*—Size 1-2 mm, density 1-2/cm.sup.2.

Flowers:

*Bud*.—Quantity per spur 4 to 5; length 8-10 mm; shape globose; color red-purple RHS 61A.

*Petals*.—Quantity per flower 5; Margins free to touching; Apex shape round; Base shape round; Length 16-18 mm; Width 15-16 mm; upper surface color white RHS 155D; Lower surface color red RHS 63A.

*Flower*.—Diameter of fully open flower 2 cm; Quantity per cluster 5.

*Sepals*.—Quantity per flower 5; Shape triangular; color green RHS 135A.

*Pedicel*.—Length 19-21 mm; Diameter 2 mm; Color greyed-purple RHS 187A.

*Pistil*.—Length 13-14 mm; Color yellow-green RHS 145C.

*Anthers*.—Quantity per flower 16; length 2 mm; pollen color yellow RHS 12B.

*Stigma*.—Size 1 mm; Color RHS 11C.

*Style*.—Length 7 mm; color yellow-green RHS 145C.

*Bloom period*.—Mid to late Season; first bloom April 12, full bloom April 19 at Lot, France.

Leaves:

*Attitude in relation to shoot*.—Outwards.

*Size*.—Length 10-11 cm; Width 5.0-6.0 cm; Length to Width Ratio 1.8-2.0.

*Margin*.—Serrate.

*Color*.—Upper green RHS 131A; lower surface green RHS 132A.

*Shape*.—Ovate; apex acuminate; base equilateral.

*Petiole*.—Length 1.8-2.2 cm; width 2 mm; color yellow-green RHS 143A.

Fruit:

*Size*.—Weight 150-180 g; diameter 75-90 mm.

*Fruit shape*.—Cylindrical.

*Position of maximum diameter*.—Top.

*Ribbing*.—Absent.

*Aperture of eye*.—Closed.

*Depth of eye basin*.—6-8 mm.

*Width of eye basin*.—25-30 mm.

*Stalk*.—Diameter 2.5 mm; length 15-20 mm; Color RHS 200B.

*Depth of stalk cavity*.—10-12 mm.

*Width of stalk cavity*.—18 mm.

*Lenticels*.—Size 0.5-0.7 mm; density 8-10/cm.sup.2.

*Bloom of skin*.—Few.

*Greasiness of skin*.—Absent.

*Ground color of skin*.—Red RHS 47A.

*Over color of skin*.—Pink-Red RHS 46A.

*Amount of over color*.—90 percent.

*Pattern of over color*.—Solid flush.

*Flesh*.—Texture juicy, firm, about 10.5 kg/cm.sup.2; color red RHS 53B.

*Seeds*.—Quantity per fruit 6-8; teardrop shape; color brown RHS 200B.

*Aroma*.—Medium.

*Harvest date*.—Late October.

Susceptibility to known diseases/pests: None.

RM-1 differs from CSR-22 as having earlier harvesting, better storage ability due to a very firm flesh that does not oxidize, and a better sugar level. See TABLE I below.

TABLE 1

| | RM-1 | CSR-22 |
|---|---|---|
| Flowering time: | Very late | Late |
| Vigor: | Medium to weak | Weak |
| Harvesting time: | Golden + 4 week | Golden + 6 week |
| Pressure kg/cm$^2$ | 7.7-8.2 | 4-5 |
| IR °Brix | 12.4-15.0 | 10-12 |
| Acidity | 12.4-14.7 g/L MA | NA |
| Density | 0.82 | NA |
| Vitamin C[1] skin | 12.7 ± 1.7 mg/100 g FW | NA |
| Storage | Good | Low |

Xeleven is an unpatented variety differing from PRI 612-1 by having later harvesting, very firm flesh, better sugar level, a complex tropical flavor and very long storage. The patent status of PRI 612-1 and Golden is unknown. Distinctions are shown in TABLE II.

TABLE II

| | Xeleven | PRI 612-1 | Golden |
|---|---|---|---|
| Flowering time: | Medium-Late | Medium | Medium |
| Vigor: | Medium | Strong | Medium |
| Harvesting time: | Golden + 5 week | Golden − 2 week | Mid September |
| Pressure kg/cm$^2$ | 9.9-10.3 | 8.5-9.5 | 6.6-7.0 |
| IR °Brix | 14.0-15.0 | 11.1-12.2 | 11.5-13.0 |
| Acidity | 7.8 g/L MA | 5.7-6.1 g/L MA | 3.8-5.1 g/L MA |
| Density | NA | NA | 0.78 |
| Vitamin C[1] flesh | NA | NA | 1.3 ± 03 mg/100 g FW |
| Storage | Very Good | Medium | Good |

What is claimed is:

1. A new and distinct apple tree substantially as shown and illustrated herein.

* * * * *